US007999934B2

(12) United States Patent
Naya et al.

(10) Patent No.: US 7,999,934 B2
(45) Date of Patent: Aug. 16, 2011

(54) SPECTROSCOPIC DEVICE AND RAMAN SPECTROSCOPIC SYSTEM

(75) Inventors: Masayuki Naya, Ashigarakami-gun (JP); Takeharu Tani, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 223 days.

(21) Appl. No.: 12/303,785

(22) PCT Filed: Jun. 7, 2007

(86) PCT No.: PCT/JP2007/061952
§ 371 (c)(1),
(2), (4) Date: Dec. 8, 2008

(87) PCT Pub. No.: WO2007/142360
PCT Pub. Date: Dec. 13, 2007

(65) Prior Publication Data
US 2010/0165334 A1 Jul. 1, 2010

(30) Foreign Application Priority Data

Jun. 8, 2006 (JP) ................................. 2006-159910
May 10, 2007 (JP) ................................. 2007-125270

(51) Int. Cl.
*G01J 3/44* (2006.01)
(52) U.S. Cl. ...................................................... 356/301
(58) Field of Classification Search .................... 356/301
See application file for complete search history.

(56) References Cited

U.S. PATENT DOCUMENTS

| 7,288,419 | B2 | 10/2007 | Naya |
| 2002/0064800 | A1 | 5/2002 | Sando et al. |
| 2004/0063214 | A1 | 4/2004 | Berlin et al. |
| 2007/0252982 | A1* | 11/2007 | Wang et al. .................. 356/301 |

FOREIGN PATENT DOCUMENTS

| CN | 1685217 A | 10/2005 |
| JP | 2002-221485 A | 8/2002 |
| JP | 2003-049205 A | 2/2003 |
| JP | 2003-294754 A | 10/2003 |
| JP | 2005-172569 A | 6/2005 |
| JP | 2006-501481 A | 1/2006 |
| WO | 2005/114298 A2 | 12/2005 |
| WO | 2006/033914 A2 | 3/2006 |

OTHER PUBLICATIONS

EP Communication, dated Apr. 8, 2010, issued in corresponding EP Application No. 07767117.0, 11 pages.
Bingler et al., "Interference enhanced surface Raman scattering of adsorbates on a silver-spacer-islands multilayer system," Molecular Physics, vol. 85, No. 3, Jun. 20, 1995, pp. 587-606, XP-008120507.

(Continued)

*Primary Examiner* — Tarifur Chowdhury
*Assistant Examiner* — Abdullahi Nur
(74) *Attorney, Agent, or Firm* — Sughrue Mion, PLLC

(57) ABSTRACT

A Raman spectroscopic device includes an optical resonator, in which a first reflecting body that exhibits semi transmissivity/semi reflectivity and has a surface which is a light scattering surface that generates Raman scattering, a transparent body, and a second reflecting body that exhibits reflectivity, are laminated in sequence one on another. The Raman spectroscopic device utilizes light absorption due to resonance to obtain a surface amplified Raman effect.

11 Claims, 11 Drawing Sheets

OTHER PUBLICATIONS

Leitner et al., "Optical properties of a metal island film close to a smooth metal surface," Applied Optics, vol. 32, No. 1, Jan. 1, 1993, pp. 102-110, XP-002574134.

Bauer et al., "Resonant nanocluster technology—from optical coding and high quality security features to biochips," Nanotechnology, vol. 14, No. 12, Dec. 1, 2003, pp. 1289-1311, XP-020067415.

CN First Office Action, dated Apr. 2, 2010, issued in corresponding CN Application No. 200780021241.2, 11 pages in English and Chinese.

The Second Office Action, dated Dec. 14, 2010, issued in corresponding CN Application No. 200780021241.2, 11 pages in English and Chinese.

* cited by examiner

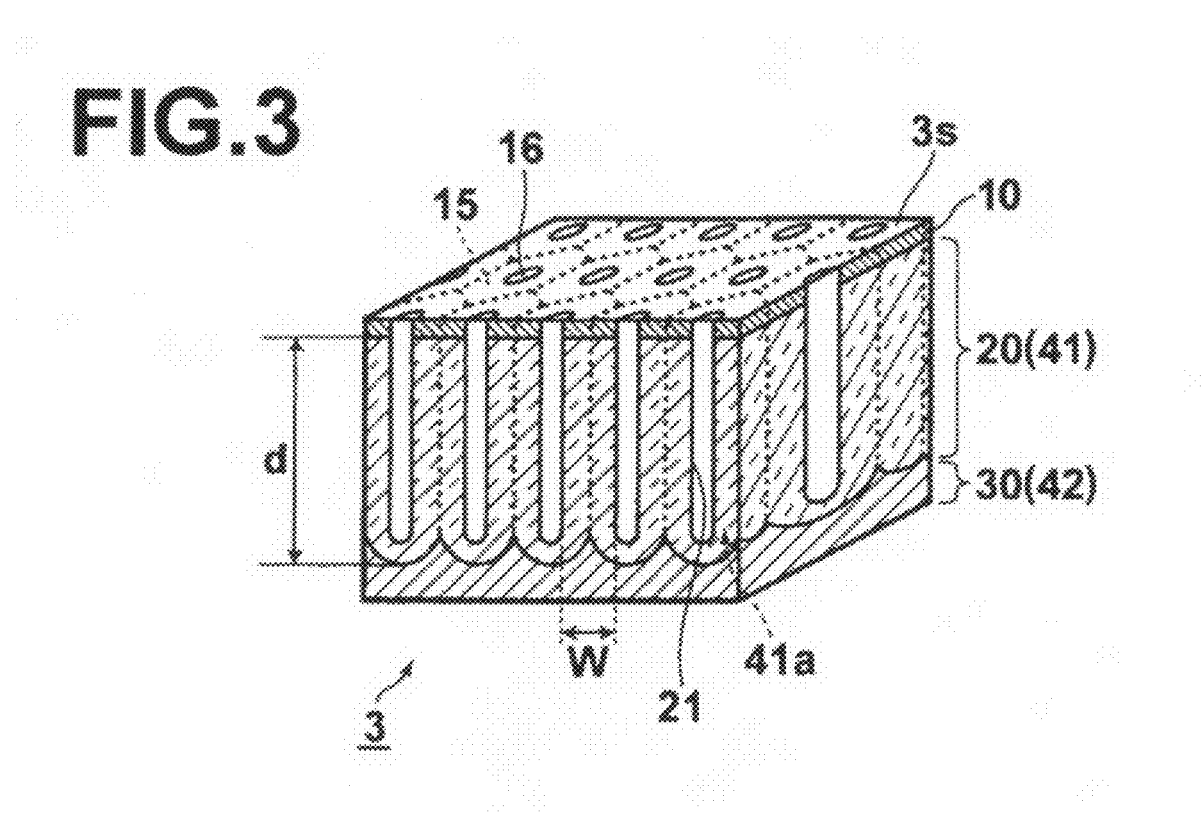

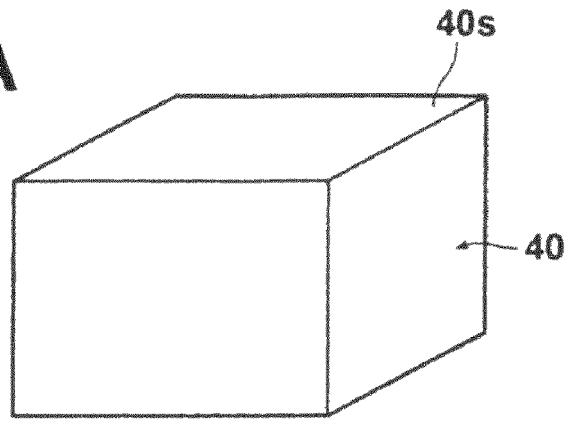
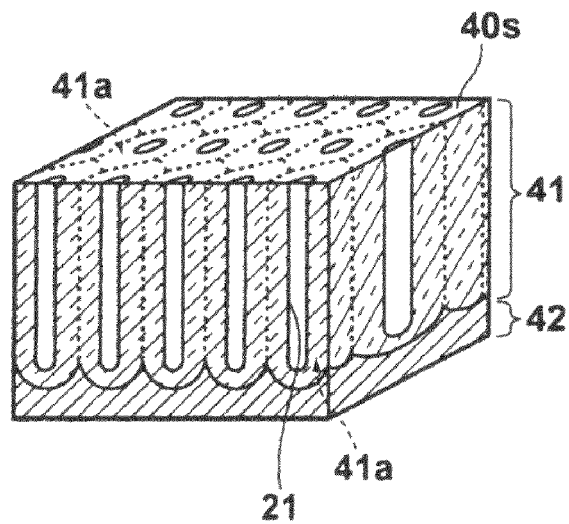
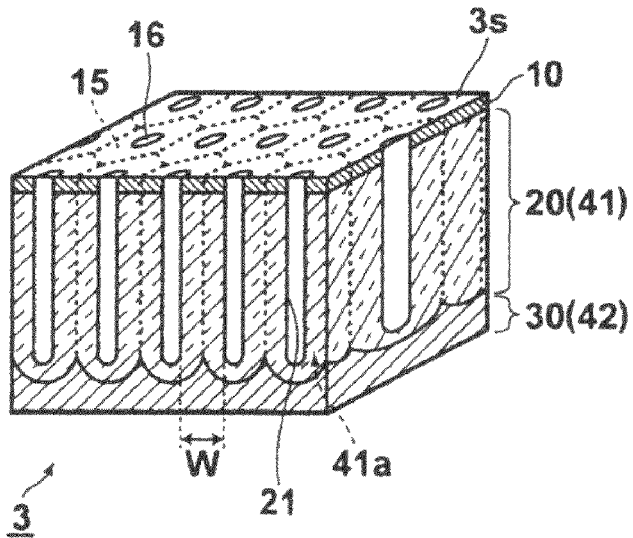

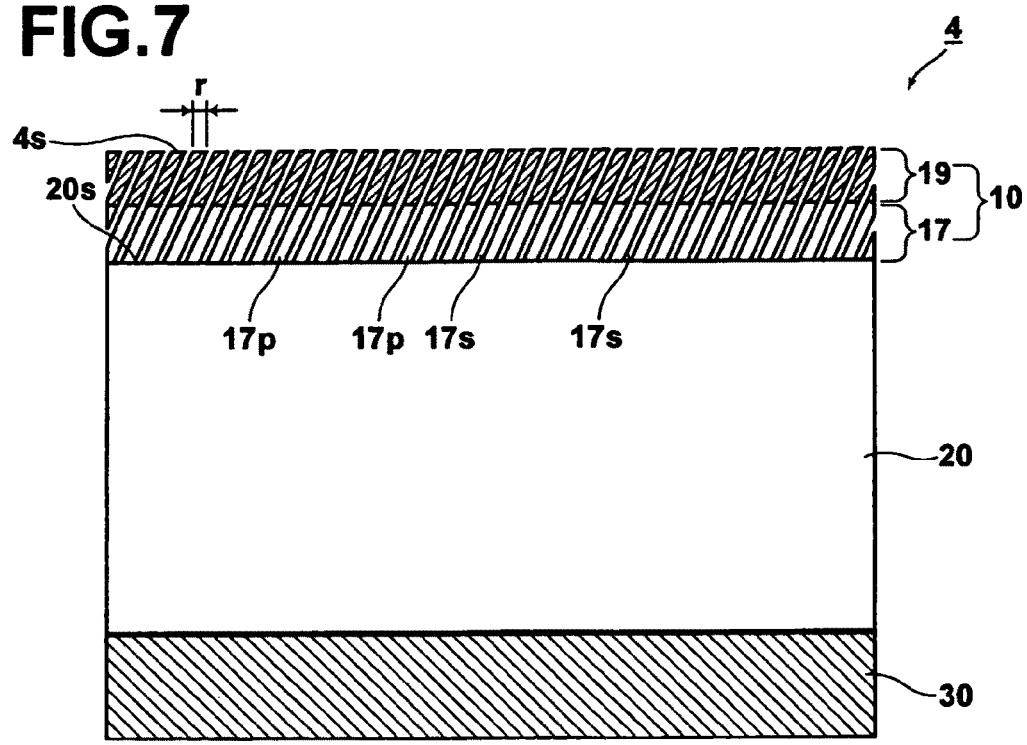
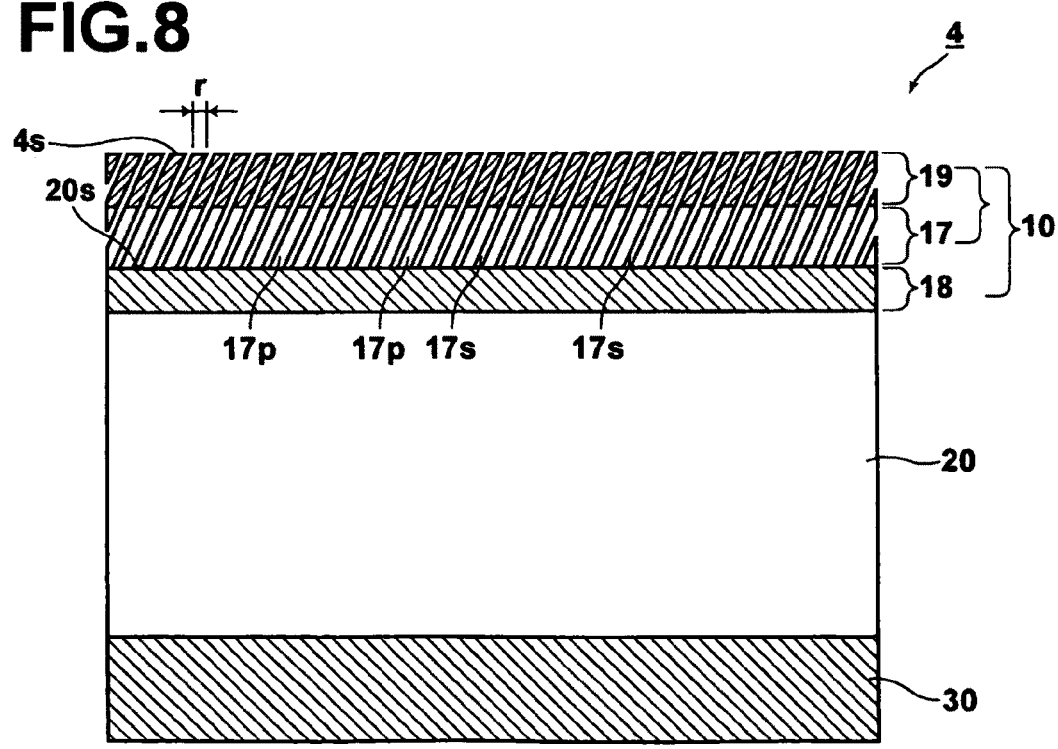

SPECTROSCOPIC DEVICE AND RAMAN SPECTROSCOPIC SYSTEM

CROSS REFERENCE TO RELATED APPLICATION

This application is a National Stage of International Application No. PCT/JP2007/061952 filed Jun. 7, 2007, claiming priority based on Japanese Patent Application Nos. 2006-159910 filed Jun. 8, 2006 and 2007-125270, filed May 10, 2007, the contents of all of which are incorporated herein by reference in their entirety.

TECHNICAL FIELD

This invention relates to a Raman spectroscopic device having a function of enhancing Raman scattering and a Raman spectroscopic system using the Raman spectroscopic device.

BACKGROUND ART

Raman spectroscopy is a method in which light of a mono-wavelength is projected onto a material and the obtained scattered light is spectroscopically (in a spectroscopic fashion) divided to obtain the Raman spectrum of Raman scattered light and is employed for, for instance, identification of the material. Since the Raman scattered light is weak, there has been developed surface enhancing Raman device where the Raman scattering is enhanced on the surface. As one of the surface enhancing Raman devices, a device using a local plasmon resonance can be shown. This device is based on the fact that when light is projected onto a metal body, especially a metal body having an irregularity of an order of nanometer, in a state where the material is in contact with the metal body, an electric field is enhanced by a local plasmon resonance and the intensity of the Raman scattered light of the sample in contact with the metal body is enhanced. It is said as the regularity of the fine structure of the metal body is higher, an electric field enhancement which is more uniform and more effective can be obtained.

As one of methods of producing a fine irregularity structure on the surface of metal body, a method where metal particles highly uniform in particle diameters are prepared and the metal particles is randomly fixed to the surface of the metal body can be shown. In Japanese Unexamined Patent Publication No. 2003-49205, there is disclosed a method of producing metal particles highly uniform in particle diameters where an organic ligand having a hydrophobic group is coordinated around metal particles, and the metal particles are solidified as the ligand is coordinated. By such a method, metal particles which are highly uniform in particle diameters and small in aggregation of the particles can be obtained.

In Japanese Unexamined Patent Publication No. 2005-172569, there are disclosed a fine structure where metal particles of an order of nanometer are positioned in regularly distributed fine holes and a Raman spectroscopic device using the fine structure.

However, the method disclosed in Japanese Unexamined Patent Publication No. 2003-49205 requires the steps of coordinating the organic ligand with the metal, solidifying the same and removing the solvent used in the step of coordinating the organic ligand with the metal and number of steps are required before fixing the fine particles to the metal body. Further, in Japanese Unexamined Patent Publication No. 2003-49205, there is not disclosed a method of regularly fixing the fine particles uniform in particle diameters to the metal body.

In a fine structure disclosed in Japanese Unexamined Patent Publication No. 2005-172569, the problem described above is overcome and a highly regular fine structure can be produced. However, in order to obtain more effective surface enhancement in the surface enhancing Raman devices, it is necessary to conform the measuring light with the resonant wavelength at which the surface enhancing Raman effect can be obtained (the wavelength will be simply referred to as "the Raman effect enhancing wavelength", hereinbelow), and in the Raman spectroscopy which requires a change of the wavelength of the measuring light according to the object material to be detected, the surface enhancing Raman devices having a Raman effect enhancing wavelength according to the wavelength of the measuring light becomes necessary. In the surface enhancing Raman devices using local plasmon resonance, a complicated design change of carrying out a precise control of the metal fine structure at each wavelength becomes necessary in order to conform the wavelength of the measuring light to the local plasmon resonant wavelength.

DISCLOSURE OF THE INVENTION

In view of the foregoing observations and description, the primary object of the present invention is to provide a Raman spectroscopic device in which the Raman effect enhancing wavelength can be more simply controlled as compared with the surface enhancing Raman device using local plasmon resonance and a Raman spectroscopic system using the Raman spectroscopic device.

In accordance with the present invention, there is provided a Raman spectroscopic device for use in Raman spectroscopy where measuring light of a particular wavelength is projected onto a sample in contact with a light scattering surface and the obtained Raman scattered light generated in the light scattering surface is spectroscopically (in a spectroscopic fashion) divided and is employed for, for instance, detecting a material in the sample comprising an optical resonator where a first reflecting body which exhibits a semi-transmissivity/semi-reflectivity and has a surface which is the light scattering surface, a transparent body and a second reflecting body which has a reflectivity are superposed in sequence one on another, whereby the intensity of the Raman scattered light is enhanced by the electric field enhanced in the light scattering surface by light absorption generated by a resonance in the optical resonator upon projection of the measuring light.

In this specification, the "semi-transmissivity/semi-reflectivity" means to have both the transmissivity and the reflectivity irrespective of the transmittance and the reflectance.

In the Raman spectroscopic device of the present invention, it is preferred that the first reflecting body has irregularity structure which is smaller than the wavelength of the measuring light to be projected onto the light scattering surface.

The expression "irregularity structure which is smaller than the wavelength of the measuring light" as used here means that the average size (the "size" as used here means "a maximum width") of the projections and the recessed parts (the "recessed parts" as used here includes a space extending through the reflecting body in the direction of thickness) and the average pitches of the projections and the recessed parts are smaller than the wavelength of the measuring light.

As a preferred embodiment of the Raman spectroscopic device of the present invention, there can be shown that in which the first reflecting body is a metal layer formed in a pattern on the surface of the transparent body.

As another preferred embodiment of the Raman spectroscopic device of the present invention, there can be shown that in which the first reflecting body is a metal layer comprising a plurality of non-aggregate metal particles fixed to the surface of the transparent body.

In this specification, the "non-aggregate metal particles" is defined to be metal particles included in either one of (1) those where the metal particles are spaced from each other without associating with each other and (2) those where the metal particles are a single particle after they bond together and never returns to the original state.

As still another preferred embodiment of the Raman spectroscopic device of the present invention, there can be shown that in which the transparent body comprises a transparent fine hole body having a plurality of fine holes which open in a surface opposed to the first reflecting body and is smaller than the wavelength of the measuring light in diameter and the first reflecting body is a metal layer having a plurality of fine holes along the surface of the transparent body. In such a structure, at least a part of the fine holes may be filled with metal or only a bottom of the fine holes may be filled with metal.

As still another preferred embodiment of the Raman spectroscopic device of the present invention, there can be shown that where the first reflecting body comprises metal column structure film having a number of substantially parallel columns extending in a non-parallel direction to the surface of the transparent body.

As still another preferred embodiment of the Raman spectroscopic device of the present invention, there can be shown that where the first reflecting body comprises dielectric column structure film having a number of substantially parallel columns extending in a non-parallel direction to the surface of the transparent body and metal film formed on the dielectric column structure film.

The Raman spectroscopic system of the present invention comprises a Raman spectroscopic device of the present invention described above, a light projecting means which projects light of a particular wavelength onto the light scattering surface of the Raman spectroscopic device and a spectral means which spectroscopically divides the light scattered by the light scattering surface, thereby obtaining spectrum of Raman scattered light.

Since the Raman spectroscopic device of the present invention comprises an optical resonator where the first reflecting body which exhibits semi-transmissivity/semi-reflectivity and has a surface which is a light scattering surface generating a Raman scattering, the transparent body and the second reflecting body which has a reflectivity are superposed in sequence one on another, and light traveling into the transparent body after transmitted by the first reflecting body repeats reflection between the first and second reflecting bodies to generate multiple reflection, whereby a multiple interference by the light reflected in the multiple reflection effectively takes place and the electric field of the optical resonator is enhanced at the resonant wavelength by the resonance generated by the multiple interference. Accordingly, the surface enhancing Raman effect is effectively obtained in the surface of the first reflecting body which is a light scattering surface.

Further, since in the Raman spectroscopic device of the present invention, the resonating wavelength changes according to the average refractive index and the thickness of the transparent body, and the Raman effect enhancing wavelength can be controlled by a simple design change where these factors are only changed. Accordingly, in accordance with the present invention, it is possible to obtain the Raman spectroscopic device having the surface enhancing Raman effect at a desired wavelength according to the application by a simple design change.

BRIEF DESCRIPTION OF THE DRAWINGS

FIG. 3 is a perspective view of a Raman spectroscopic device in accordance with a third embodiment of the present invention, FIGS. 4A to 4C are views showing the process of producing the Raman spectroscopic device shown in FIG. 3, FIG. 7 is a cross-sectional view in the direction of thickness showing a Raman spectroscopic device in still another preferred form of a fourth embodiment of the present invention, FIG. 8 is a cross-sectional view in the direction of thickness showing a Raman spectroscopic device in still another preferred form of a fourth embodiment of the present invention.

BEST MODE FOR CARRYING OUT THE INVENTION

First Embodiment of the Raman Spectroscopic Device

Figure 1A:
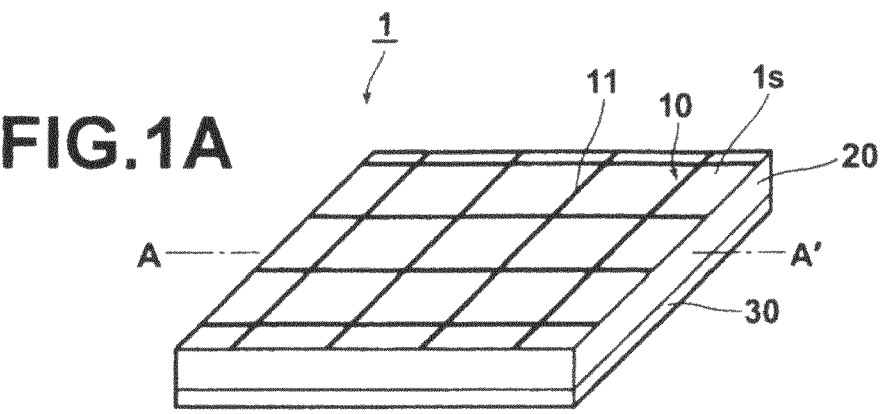
FIG. 1A is a perspective view of a Raman spectroscopic device in accordance with a first embodiment of the present invention.

A Raman spectroscopic device in accordance with a first embodiment of the present invention will be described with reference to FIGS. 1A and 1B, hereinbelow. FIG. 1A is a perspective of the first embodiment and FIG. 1B is a cross-sectional view of the same (taken along line A-A').

Figure 1B:
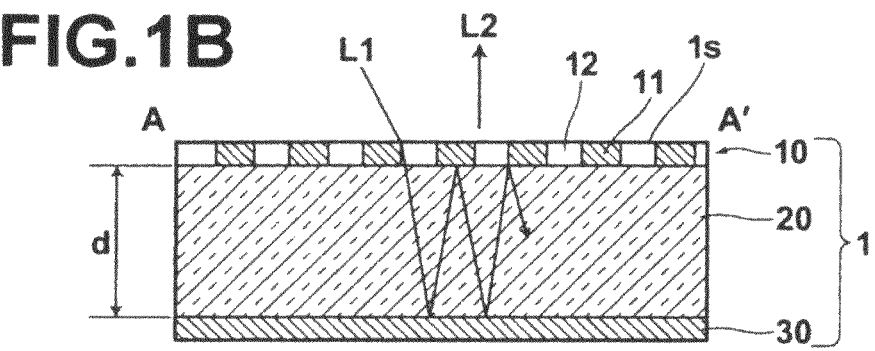
FIG. 1B is a cross-sectional view of the same.

As shown in FIGS. 1A and 1B, the Raman spectroscopic device 1 in accordance with this embodiment comprises in sequence, from the incident side (from upward in FIGS. 1A and 1B) of measuring light L1, a first reflecting body 10 which exhibits semi-transmissivity/semi-reflectivity and has a surface which is a light scattering surface is generating a Raman scattering, a transparent body 20 and a second reflecting body 30 which has a reflectivity. The measuring light L1 is mono-wavelength light and the wavelength of the measuring light L1 is selected according to the material to be detected.

The transparent body 20 comprises a transparent flat substrate while the first reflecting body 10 comprises a metal layer where fine metal cable 11 is formed in a regular grid pattern on one side of the transparent body 20 and the second reflecting body 30 comprises a solid metal layer where fine metal formed on the other side of the transparent body 20.

The transparent body 20 may be formed of any suitable material, and for instance, may be formed of a transparent ceramics such as glass or alumina or a transparent resin such as acrylic resin or polycarbonate resin.

The first and second reflecting bodies 10 and 30 may be formed of any suitable reflective metal and may be formed of Au, Ag, Cu, Al, Pt, Ni, Ti or their alloys. The first and second reflecting bodies 10 and 30 may include not smaller than two kinds of these reflective metals.

The second reflecting body 30 which is a solid metal layer can be formed by, for instance, a metal vapor deposition.

The first reflecting body 10 can be formed, for instance, by carrying out the known photolithography after a solid metal layer is formed by, for instance, the metal vapor deposition.

The first reflecting body 10 exhibits a light transmissivity since it has a plurality of patterned spaces 12 though formed of reflective metal and after all exhibits a semi-transmissivity/semi-reflectivity. The line width and the pitches of the fine metal cable 11 of the first reflecting body 10 are smaller than the wavelength of the measuring light L1, and the first reflecting body 10 has an irregularity smaller than the wavelength of the measuring light L1. When the irregularity is smaller than the wavelength of the light, the first reflecting body behaves as film to light and exhibits a semi-transmissivity/semi-reflectivity having an electromagnetic mesh shielding function.

The Raman spectroscopic device in accordance with this embodiment is a device having a surface enhancing Raman effect, where the electric field is strengthened on the light scattering surface is of the first reflecting body 10, and the sample can be analyzed by placing a sample or a sample cell in contact with the light scattering surface 1s.

The pitches of the fine metal cable 11 may be any so long as they are smaller than the wavelength of the measuring light L1 and when visible light is employed as the measuring light L1, the pitches of the fine metal cable 11 are preferably not larger than, for instance, 200 nm. The pitches of the fine metal cable 11 are preferably as small as possible. The line width of the fine metal cable 11 may be any so long as it is smaller than the wavelength of the measuring light L1 and the line width of the fine metal cable 11 is preferably as small as possible. The line width of the fine metal cable 11 is preferably not larger than an average free stroke of the electrons which are vibrated by light, and specifically, the line width of the fine metal cable 11 is preferably not larger than 50 nm and more preferably not larger than 30 nm.

The thickness of the transparent body 20 may be any, and preferably not larger than 300 nm in that absorption peak wavelength in a visible wavelength region by the multiple interference is a single and easy to detect, while preferably not smaller than 100 nm in that a multiple interference effectively takes place, and absorption peak wavelengths by the multiple interference are easy to detect in a visible wavelength region.

In the Raman spectroscopic device in accordance with this embodiment, the resonant wavelength can be changed according to a thickness of the transparent body 20 and an average refractive index in the transparent body 20. A thickness of the transparent body 20, an average refractive index in the transparent body 20 and the resonant wavelength substantially satisfies the following formula (1), and accordingly, when the Raman spectroscopic devices are the same in the average refractive index in the transparent body 20, the resonant wavelength can be changed by only changing the thickness of the transparent body 20.

$$\lambda \approx 2nd/(m+1) \qquad (1)$$

wherein d represents the thickness of the transparent body 20, $\lambda$ represents the resonant wavelength, n represents the average refractive index in the transparent body 20 and m represents an integer.

When the transparent body 20 comprises a light transmitting fine hole member as in the third embodiment described later, "the average refractive index in the transparent body 20" means the average of the refractive index in the light transmitting fine hole member and the refractive index of the material in the fine holes (when the fine holes are not filled with a particular material, "the material in the fine holes" is air, and when the fine holes are filled with a particular material, "the material in the fine holes" is the particular material in the fine holes and/or a mixture of air and the particular material in the fine holes.)

Further, though the refractive index is represented by a complex refractive index when the material absorbs light, since the complex part is 0 in the transparent body 20 and even when the transparent body 20 has fine holes, the influence by the material in the fine holes is small, the formula (1) is shown as a simple refractive index without a complex part.

Though varies depending upon the physical properties and/or the surface state of the first and second reflecting bodies 10 and 30, since the value of the change is small as compared with the influence by the thickness of the transparent body 20 and the average refractive index in the transparent body 20, the resonant wavelength can be determined in a precision of order of several nm according to the above formula (1).

As shown in FIG. 1B, when the measuring light L1 impinges upon the Raman spectroscopic device 1, the measuring light L1 is partly reflected by the surface of the first reflecting body 10 (not shown) and partly passes through the first reflecting body 10 to enter the transparent body 20 according to the transmissivity or the reflectance of the first reflecting body 10. Light entering the transparent body 20 is repeatedly reflected between the first and second reflecting bodies 10 and 30. That is, the Raman spectroscopic device 1 is of resonant structure where a multiple reflection takes place between the first and second reflecting bodies 10 and 30. Accordingly, a multiple interference by multiple reflection light takes place in the transparent body 20 and resonates at a particular wavelength satisfying the resonant conditions to exhibit an absorption characteristics where the light at the resonant wavelength is absorbed. Then, emanation light L2 different from the measuring light L1 in the physical properties is emanated according to the absorption characteristics. Further, inside the device, the electric field is enhanced according to the absorption characteristics and the surface enhancing Raman effect can be obtained at the light scattering surface 1s.

In the Raman spectroscopic device 1, it is preferred that the device structure is formed by taking an optical impedance matching so that the number of the multiple reflection (finesse) in the transparent body 20 is maximized. Such arrangement is preferable in that the absorption peaks become sharp and a more effective Raman enhancing can be obtained.

In the Raman spectroscopy, it is necessary to change the wavelength of the measuring light to be projected onto a sample according to the sample and in a Raman spectroscopic device where the Raman enhancing wavelength is caused to conform to the wavelength of the measuring light, an effective surface enhancing Raman effect can be obtained. Accordingly, it is preferred to design a Raman spectroscopic device according to the wavelength of the measuring light. However, control of the Raman enhancing wavelength requires complicated process, for instance, in the case of a surface enhancing Raman spectroscopic device using local plasmon resonance since a precise control of the size of the fine structure of metal is necessary.

In the Raman spectroscopic device 1 of this embodiment, since the resonant wavelength changes according to the thickness and the average refractive index of the transparent body 20 as shown in formula (1), the Raman effect enhancing wavelength can be controlled by a simple design change where these factors are only changed. Accordingly, in accordance with this embodiment, the Raman spectroscopic device which has the surface enhancing Raman effect at a desired wavelength according to the application thereof can be easily obtained without a complicated device design.

In the Raman spectroscopic device 1 of this embodiment, since a multiple interference effectively takes place and a strong absorption to light of a particular wavelength takes place, the surface enhancing Raman effect is larger than the Raman spectroscopic device using local plasmon resonance (for instance, not smaller than 100 times) and a high-precision analysis can be realized.

In the Raman spectroscopic device 1 of this embodiment, since further the first reflecting body 10 is of metal having free electrons and the first reflecting body 10 has an irregularity smaller than the wavelength of the measuring light L1, local plasmon resonance can take place in the first reflecting body 10.

Local plasmon resonance is a phenomenon where the free electrons of metal resonate with the electric field of light and an electric field is generated. It is said that especially in a metal layer having a fine irregularity, a strong electric field is generated around projections when free electrons on the projections resonate with the electric field of light and vibrates and the local plasmon resonance effectively takes place. In this embodiment, since the first reflecting body 10 has an irregularity smaller than the wavelength of the measuring light L1 as described above, the local plasmon resonance effectively takes place.

At the wavelength where the local plasmon resonance is generated, scattering and/or absorption of the measuring light L1 is significantly enhanced, and the electric field is enhanced at the light scattering surface is as the resonance by the above multiple interference. The wavelength where the local plasmon resonance is generated (resonance peak wavelength) and the degree of scattering and/or absorption of the measuring light L1 depend upon the size of irregularity on the surface of the Raman spectroscopic device 1, the kind of metal, the refractive index of the sample in contact with the surface and the like.

The absorption peaks by the multiple interference and by the local plasmon resonance appear sometimes at different wavelengths and sometimes at a wavelength.

Though the first and second reflecting bodies 10 and 30 may be formed of any suitable reflective material other than metal, that the first reflecting body 10 is formed of metal is preferable in that the surface enhancing Raman effect by the local plasmon resonance can also be obtained.

In this embodiment, both the resonance by the multiple interference and the local plasmon resonance are generated and the surface enhancing Raman effects generated by phenomena independent of each other are obtained as described above. However, it is conceivable that the surface enhancing Raman effect is enhanced by mutual action of these phenomena or a phenomenon peculiar to the structure of the device described above.

Though the case where the first reflecting body 10 is in a regular grid pattern has been described in this embodiment, the first reflecting body 10 is in any pattern and it may be even in a random pattern. However, that the regularity in structure is higher is preferred in that higher the in-plane uniformity of the resonant structure is, and the characteristics are more concentrated.

Second Embodiment of the Raman Spectroscopic Device

Figure 2A:
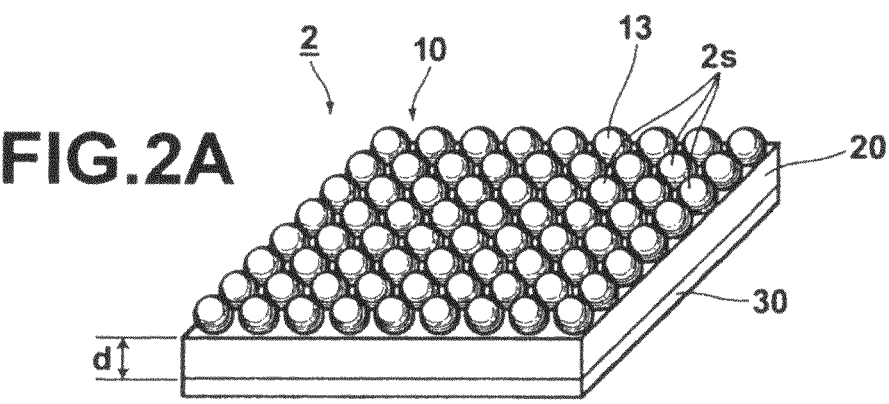
FIG. 2A is a perspective view of a Raman spectroscopic device in accordance with a second embodiment of the present invention.
Figure 2B:
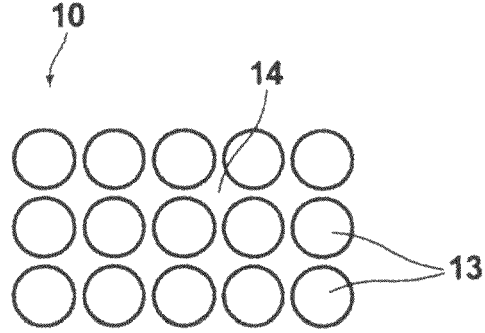
FIG. 2B is a plan view of the same.

A Raman spectroscopic device of a second embodiment of the present invention will be described with reference to FIGS. 2A and 2B, hereinbelow. FIG. 2A is a perspective view similar to FIG. 1A of the first embodiment and FIG. 2B is a plan view of a Raman spectroscopic device. In this embodiment, the elements analogous to those in the first embodiment will be given the same reference numerals and will not be described.

As shown in FIGS. 2A and 2B, the Raman spectroscopic device 2 in accordance with this embodiment comprises similarly to the first embodiment, in sequence from the incident side of measuring light L1, a first reflecting body 10 which exhibits semi-transmissivity/semi-reflectivity and has a surface which is a light scattering surface 2s generating a Raman scattering, a transparent body 20 and a second reflecting body 30 which has a reflectivity.

The Raman spectroscopic device 2 in accordance with this embodiment differs from that in accordance with the first embodiment in that the first reflecting body 10 is formed of a plurality of non-aggregate metal particles 13 of substantially the same diameters which are regularly arranged in matrix on the surface of the transparent body 20 and fixed there, whereas the first reflecting body 10 in the first embodiment is a metal layer formed in a pattern.

In this embodiment, similarly to the first embodiment that the regularity in structure is higher is preferred in that higher the in-plane uniformity of the resonant structure is, and the characteristics are more concentrated. When the metal particles 13 includes aggregate metal particles, the first reflecting body is formed of partly aggregate metal particles where a number of metal particles aggregate and partly non-aggregate metal particles and the regularity in structure of the first reflecting body is apt to be lowered. Whereas, since the metal particles 13 are non-aggregate metal particles in this embodiment, the first reflecting body 10 can be easily higher in uniformity of the structure as compared with when the metal particles 13 includes aggregate metal particle.

The metal particles 13 may be formed of any suitable, and, for instance, it may be formed of the same metal for the first reflecting body 10 of the first embodiment.

Further, since the metal particles 13 are non-aggregate metal particles, as previously mentioned, they belong to either one of (1) those where the metal particles are spaced from each other without associating with each other and (2) those where the metal particles are a single particle after they bond together and never returns to the original state.

As the first reflecting body 10 comprising a metal layer formed by a plurality of secured metal particles 13 defined in (1), there can be shown a metal layer where a plurality of metal particles 13 are arranged so that they are spaced from each other by a distance not smaller than a predetermined distance not to associate with each other. In this metal layer, the metal particles 13 may be either randomly or substantially regularly arranged.

As a metal layer where the metal particles 13 are randomly arranged, there can be shown a metal layer which is formed in an island pattern by a bias sputtering.

As a metal layer where the metal particles 13 are substantially regularly arranged, there can be shown those where metal particles 13 which are like a dot, mesh, or a needle or in a bow-tie array are patterned to be substantially regularly arranged. Patterning in these cases can be realized, for instance, by a method like lithography, or focusing ion beam method (FIB method) using processing or self-organizing.

As the first reflecting body 10 where a plurality of metal particles 13 are secured as defined in (2), there can be shown those where metal particles 13 are integrated in the step of metal growth by fusion or plating and cannot be returned to the state before integration.

Further, the first reflecting body 10 can be formed by, for instance, applying dispersion of the metal particles 13 by spin coating or the like to the surface of the transparent body 20, and drying it. It is preferred that the dispersion includes a binder such as resin or protein so that the metal particles 13 are fixed to the surface of the transparent body 20 by way of the binder. When protein is employed as the binder, it is possible to fix the metal particles 13 to the surface of the transparent body 20 by the use of the bonding reaction between the proteins.

The first reflecting body 10 exhibits a light transmissivity since it has a plurality of inter-particle spaces 14 which are void though formed of reflective metal and after all exhibits a semi-transmissivity/semi-reflectivity. The diameter and the pitch of the metal particles 13 are designed to be smaller than the wavelength of the measuring light L1, and the first reflecting body 10 has an irregularity smaller than the wavelength of the measuring light L1. Since being smaller than the wavelength of the light, the first reflecting body 10 behaves as film to light and exhibits a semi-transmissivity/semi-reflectivity having an electromagnetic mesh shielding function also in this embodiment.

Also the Raman spectroscopic device 2 of this embodiment is a device where an electric field is enhanced at the light scattering surface 2s of the first reflecting body 10 to obtain the surface enhancing Raman effect and the sample can be analyzed by placing a sample or a sample cell in contact with the light scattering surface 2s.

The pitches of the metal particles 13 may be any so long as they are smaller than the wavelength of the measuring light L1 and when visible light is employed as the measuring light L1, the pitches of the metal particles 13 are preferably not larger than, for instance, 200 nm. The pitches of the metal particles 13 are preferably as small as possible. The diameter of the metal particles 13 may be any and the diameter of the metal particles 13 is preferably as small as possible. The diameter of the metal particles 13 is preferably not larger than an average free stroke of the electrons which are vibrated in metal by light, and specifically, the diameter of the metal particles 13 is preferably not larger than 50 nm and more preferably not larger than 30 nm.

As in the first embodiment, also in this embodiment, light which passes through the first reflecting body 10 and enters the transparent body 20 is repeatedly reflected between the first and second reflecting bodies 10 and 30 and a multiple interference by multiple reflection light takes place and resonates at a particular wavelength satisfying the resonant conditions. By the resonance, light at the resonant wavelength is absorbed and the electric field inside the device is enhanced and the surface enhancing Raman effect can be obtained at the light scattering surface 2s. In the Raman spectroscopic device 1 of this embodiment, since the resonant wavelength changes according to the thickness and the average refractive index of the transparent body 20 as in the first embodiment, a higher surface enhancing Raman effect (for instance, not smaller than 100 times) can be obtained at a wavelength according to these factors.

The Raman spectroscopic device 1 of this embodiment is basically the same as the first embodiment except that the first reflecting body 10 is of the metal particle layer and accordingly, exhibits the same effect as the first embodiment.

Though the case where the first reflecting body 10 comprises a metal layer where a plurality of substantially the same diameter metal particles are regularly arranged in a matrix has been described in this embodiment, the first reflecting body 10 may be distributed and may be in any pattern. The first reflecting body 10 may be even in a random pattern.

Third Embodiment of the Raman Spectroscopic Device

A Raman spectroscopic device of a third embodiment of the present invention will be described with reference to FIGS. 3 and 4A to 4C, hereinbelow. FIG. 3 is a perspective view of a Raman spectroscopic device and FIGS. 4A to 4C are views showing the manufacturing steps of the Raman spectroscopic device. In this embodiment, the elements analogous to those in the first embodiment will be given the same reference numerals and will not be described.

As shown in FIG. 3, the Raman spectroscopic device 3 in accordance with this embodiment comprises similarly to the first embodiment, in sequence from the incident side of measuring light L1, a first reflecting body 10 which exhibits semi-transmissivity/semi-reflectivity and has a surface which is a light scattering surface 3s generating a Raman scattering, a transparent body 20 and a second reflecting body 30 which has a reflectivity.

In this embodiment, different from the first embodiment, the transparent body 20 is formed of metal oxide ($Al_2O_3$) 41 obtained by anodic-oxidizing a part of anodic-oxidized metal (Al) 40 shown in FIG. 4A and the second reflecting body 30 is formed of a non-anodic-oxidized part (Al) 42 of the anodic-oxidized metal (Al) 40. The second reflecting body 30 has a reflectivity.

In this embodiment, the transparent body 20 is a light transmitting fine hole body provided with a plurality of substantially straight fine holes 21 extending from the first reflecting body side to the second reflecting body side. The plurality of fine holes 21 are open at the face on first reflecting body side and are closed at the face on second reflecting body side. In the transparent body 20, each of the plurality of fine holes 21 has a diameter smaller than the wavelength of the measuring light L1 and the plurality of fine holes 21 are arranged substantially regularly at pitches smaller than the wavelength of the measuring light L1.

The anodic oxidation can be carried out by dipping the anodic-oxidized metal 40 (as the anode) in an electrolysis solution together with the cathode, and imparting an electric voltage across the anode and the cathode. Though the shape of the anodic-oxidized metal 40 is not limited, it is preferred that the anodic-oxidized metal 40 be like a plate or the like in shape. Those with a supporter such as those where films of anodic-oxidized metal 40 is formed on a supporting body in layers may be used. As the cathode, for instance, carbon or aluminum is used. As the electrolysis solution, an acidic electrolysis solution including but not limited to one or more of sulfuric acid, phosphoric acid, chromic acid, oxalic acid, sulfamic acid, benzensulfonic acid or amidosulfonic acid may be preferably used.

As shown in FIGS. 4A to 4C, when anodic-oxidizing anodic-oxidized metal 40, the oxidization progresses from a surface 40s substantially in perpendicular to the surface 40s and metal oxide ($Al_2O_3$) 41 is formed. The metal oxide 41 formed by the anodic oxidation is of structure where number of fine columns 41a regular hexagonal in plan are arranged without a space therebetween. At substantially the center of each fine column 41a, the fine hole 21 extending substantially straight in the direction of depth from the surface 40s opens, and the base of each fine column 41a is rounded in shape. The structure of the metal oxide body formed by the anodic oxidation is disclosed, for instance, in "Preparation of mesoporous Alumina by Anode Oxidation and Application thereof to functional Material" by H. Masuda, Material Technology, vol. 15, No. 10, p. 34, 1997.

As suitable conditions under which the anode-oxidation is to be carried out to form the regularly arranged metal oxide body 41, conditions that the concentration of the electrolysis solution is 0.5M, the temperature of the electrolysis solution is 14 to 16° C., and the electric voltage to be imparted across the anode and the cathode is 40 to 40±0.5 V when oxalic acid is employed as the electrolysis solution can be shown. The fine holes 21 formed under these conditions are 5 to 200 nm in diameter and 10 to 400 nm in pitches.

In this embodiment, the first reflecting body 10 is formed by, for instance, metal deposition to the transparent body 20 and comprises a metal layer formed along the surface contour of the transparent body 20. Since, no metal film is formed in the part of the transparent body in which the fine holes 21 open, the first reflecting body 10 is of structure where number of fine metal bodies 15 each of which has a fine hole 16 at substantially the center thereof and is a regular hexagonal in plan are arranged without a space therebetween. Since fine holes 16 of the first reflecting body 10 is formed in the same pattern as the fine holes 21 of the transparent body 20, each of the plurality of fine holes 16 has a diameter smaller than the wavelength of the measuring light L1 and the plurality of fine holes 16 are arranged substantially regularly at pitches smaller than the wavelength of the measuring light L1. Even if metal is deposited on the bottom of the fine holes 21 when the first reflecting body 10 is formed, it arises no problem.

The first reflecting body 10 exhibits a light transmissivity since it has a plurality of fine holes 16 each of which is a vacant spaces though formed of reflective metal and after all exhibits a semi-transmissivity/semi-reflectivity. Since comprising number of substantially regularly arranged fine metal bodies 15 each of which has a fine hole 16 at substantially the center thereof, is smaller than the wavelength of the measuring light L1 and is a regular hexagonal in plan, the first reflecting body 10 has an irregularity smaller than the wavelength of the measuring light L1. Since the irregularity is smaller than the wavelength of the light, the first reflecting body 10 behaves as film to light and exhibits a semi-transmissivity/semi-reflectivity having an electromagnetic mesh shielding function also in this embodiment.

Also the Raman spectroscopic device 3 of this embodiment is a device where an electric field is enhanced at the light scattering surface 3s of the first reflecting body 10 to obtain the surface enhancing Raman effect and the sample can be analyzed by placing a sample or a sample cell in contact with the light scattering surface.

The pitches of the metal bodies 15 (pitches of the fine holes 16) may be any so long as they are smaller than the wavelength of the measuring light L1 and when visible light is employed as the measuring light L1, the pitches of the metal bodies 15 are preferably not larger than, for instance, 200 nm. The pitches of the metal bodies 15 are preferably as small as possible.

Spaces between adjacent fine holes 16 (the width W of metal bodies 15 between adjacent fine holes 16) may be any and is preferably as small as possible. The width W corresponds to the width of the fine metal cable hand the metal particles 13 in the first and second embodiments. The width W is preferably not larger than an average free stroke of the electrons which are vibrated in metal by light, and specifically, the width W is preferably not larger than 50 nm and more preferably not larger than 30 nm.

In the Raman spectroscopic device 3 of this embodiment, since the second reflecting body 30 is formed of a non-anodic-oxidized part (Al) 42 of the anodic-oxidized metal (Al) 40, different from the first and second embodiments, the second reflecting body 30 is provided with a fine irregularities so that the local plasmon resonance takes place also in the second reflecting body 30 as in the first reflecting body 10.

In the Raman spectroscopic device 3 of this embodiment, metal loaded on the bottom of the fine holes 21 arises no problem. Metal loaded on the bottom of the fine holes 21 may be deposited on the bottom of the fine holes 21 when the first reflecting body 10 is formed. In this case, since the metal is loaded on the bottom of fine holes 21 which are formed in the fine columns 41a of the light transmissible metal oxide and are substantially regularly arranged in the device, a more effective local plasmon resonance takes place in the device and a high electric field enhancing effect can be obtained at a local plasmon resonant wavelength.

The metal loaded on the bottom of the fine holes 21 may be any so long as it is metal as the first reflecting body, and is preferably gold (Au), silver (Ag), copper (Cu), nickel (Ni) or titanium (Ti) and gold (Au) and silver (Ag) is especially preferable. In this case, since a local plasmon resonance takes place on the surface of the first reflecting body and on the bottom of the fine holes 21, it is preferred that metal loaded on the bottom of the fine holes 21 be of the same kind as the metal of the first reflecting body in order to obtain a more effective local plasmon resonance.

As in the first embodiment, also in this embodiment, light which passes through the first reflecting body 10 and enters the transparent body 20 is repeatedly reflected between the first and second reflecting bodies 10 and 30 and a multiple interference by multiple reflection light takes place and resonates at a particular wavelength satisfying the resonant conditions. By the resonance, light at the resonant wavelength is absorbed and the electric field inside the device is enhanced and the surface enhancing Raman effect can be obtained at the light scattering surface 3s. Since the resonant wavelength changes according to the thickness and the average refractive index of the transparent body 20 as in the first embodiment, a higher surface enhancing Raman effect (for instance, not smaller than 100 times) can be obtained at a wavelength according to these factors.

Further in this embodiment, since an effective local plasmon resonance takes place at the bottoms of the fine holes 21, a surface enhancing Raman effect by a higher local plasmon resonance as compared with the Raman spectroscopic devices of the first and second embodiments can be obtained.

The Raman spectroscopic device 3 of this embodiment is basically the same as the first embodiment except that the transparent body 20 comprises a light transmissible fine hole member having a plurality of fine holes 21 open in the face facing the first reflecting body 10 and the first reflecting body 10 comprises a metal layer formed along the surface contour of the transparent body 20 and accordingly, exhibits the same effect as the first embodiment.

Since being produced on the basis of the anodic oxidation, the Raman spectroscopic device 3 of this embodiment is preferred in that a Raman spectroscopic device 3 where the fine holes 21 of the transparent body 20 and the fine holes 16 of the first reflecting body 10 are substantially regularly arranged can be easily produced. However, these fine holes may be randomly arranged.

Though metal is filled in only the bottom of the fine holes 21 in this embodiment, it is possible to fill metal wholly or partly inside the fine holes 21. When metal is wholly filled inside the fine holes 21, though no electric field enhancement by absorption of interference inside the device takes place since the first reflecting body becomes reflective, the metal particles are substantially regularly arranged on the light scattering surface of the first reflecting body 10 and an effective local plasmon resonance is generated on the light scattering surface 3s, whereby the electric field is enhanced and the surface enhancing Raman effect can be obtained.

Though as a main component of the anodic-oxidized metal 40 used in production of the transparent body, only Al is shown in this embodiment, any metal can be used so long as it can be anodic-oxidized and the metal oxide to be generated is light transmissible. Other than Al, Ti, Ta, Hf, Zr, Si, In, Zn or the like may be used. The anodic-oxidized metal 40 may include two or more kinds of metals which can be anodic-oxidized.

Fourth Embodiment of the Raman Spectroscopic Device

Figure 5:
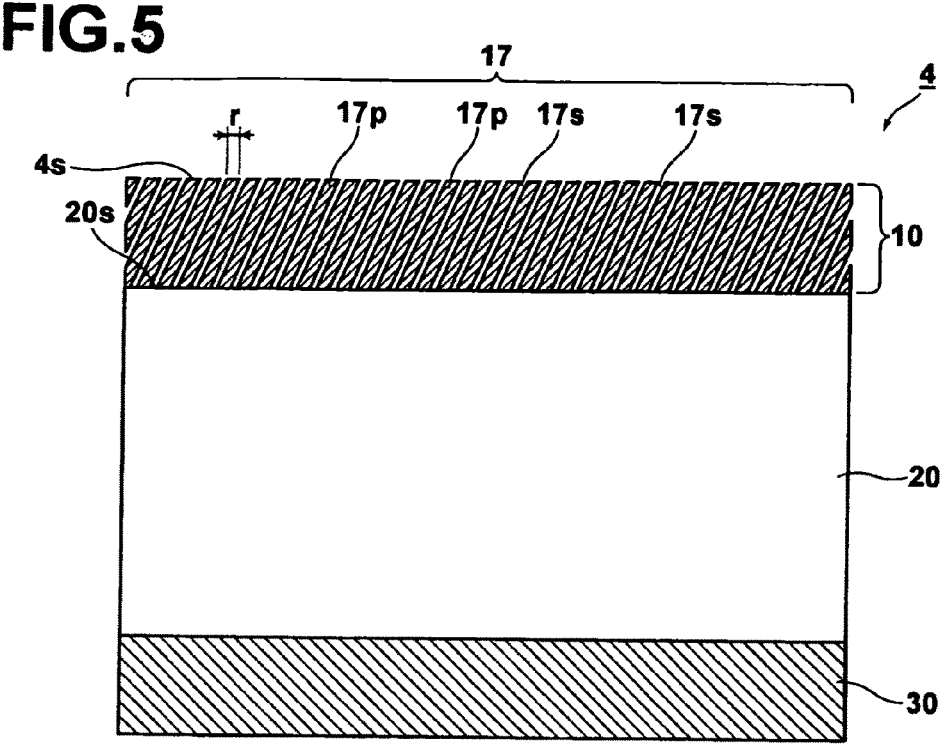
FIG. 5 is a cross-sectional view in the direction of thickness showing a Raman spectroscopic device in accordance with a fourth embodiment of the present invention.

A Raman spectroscopic device of a fourth embodiment of the present invention will be described with reference to FIG. 5, hereinbelow. FIG. 5 is a cross-sectional view in the direction of thickness showing a Raman spectroscopic device in accordance with a fourth embodiment of the present invention. In this embodiment, the elements analogous to those in the first embodiment will be given the same reference numerals and will not be described.

As shown in FIG. 5, the Raman spectroscopic device 4 of this embodiment comprises similarly to the first embodiment, in sequence from the incident side of measuring light L1, a first reflecting body 10 which exhibits semi-transmissivity/semi-reflectivity and has a surface which is a light scattering surface 4s generating a Raman scattering, a transparent body 20 and a second reflecting body 30 which has a reflectivity.

The Raman spectroscopic device in accordance with this embodiment differs from that in accordance with the first embodiment in that the first reflecting body 10 comprises a patterned metal layer in the first embodiment, the first reflecting body 10 in this embodiment comprises column structure film 17 having a number of substantially parallel columns 17p extending in a non-parallel direction to the surface 20s of the transparent body 20.

The column structure film 17 in metal film may be any so long as it is metal and metal similar to those for the first reflecting body 10 may be shown. The column structure film 17, though it is metal film, exhibits a light transmissivity since it has a plurality of vacant spaces between adjacent columns 17p and after all exhibits a semi-transmissivity/semi-reflectivity. Since the diameter r of the column and the density of the vacant spaces have been designed so that the first reflecting body 10 has irregularity structure which is smaller than the wavelength of measuring light L1. Accordingly, the first reflecting body 10 behaves as film to light and exhibits a semi-transmissivity/semi-reflectivity having an electromagnetic mesh shielding function.

Though the column structure film 17 may be formed of in any method, there can be shown a gas phase growth method such as sputtering or CVD (chemical vapor deposition). Though a number of columns 17p forming the column structure film 17 must only extend in non-parallel to the surface of the transparent body 20, the columns 17p preferably extend in the range of 90°±15° to the surface of the transparent body 20. As described above, it is preferred that adjacent columns 17p be spaced from each other by a void 17s. When the column structure film 17 is formed of in above described method, it is further preferred that the direction of the growth of the columns 17p be a direction but 90° in the above range. Accordingly, it is preferred that the column structure film 17 be formed by a bias sputtering. However, when the thickness of the film is sufficiently small, the column structure film 17 has light transmissivity even if it does not have a sufficient amount of void 17s.

The thickness of the column structure film 17 may be any so long as the column structure film 17 exhibits a semi-transmissivity/semi-reflectivity. Though the length of the columns 17p may be any, when the length of the columns 17p is in the range of 30 to 500 nm, the column structure film 17 can have a semi-transmissivity/semi-reflectivity with a sufficient amount of void 17s irrespective of the direction of growth of the columns 17p to the surface of the transparent body 20.

Also the Raman spectroscopic device 4 of this embodiment is a device where an electric field is enhanced at the light scattering surface 4s of the first reflecting body 10 to obtain the surface enhancing Raman effect and the sample can be analyzed by placing a sample or a sample cell in contact with the light scattering surface 4s.

Though the diameter r of the columns 17p and the density of the voids 17s may be any so long as the first reflecting body 10 has irregularity structure which is smaller than the wavelength of measuring light L1, when visible light is employed as the measuring light L1, the irregularity not larger than, for instance, 200 nm is preferably provided to the first reflecting body 10. Also in this embodiment, since the higher the regularity in structure is, the higher in-plane uniformity of the resonant structure is, it is preferred that the voids 17s be substantially uniformly distributed.

The diameter of the columns 17p may be any and is preferably as small as possible. The diameter of the columns 17p is preferably not larger than an average free stroke of the electrons which are vibrated in metal by light, and specifically, the diameter of the columns 17p is preferably not larger than 50 nm and more preferably not larger than 30 nm.

As in the first embodiment, also in this embodiment, light which passes through the first reflecting body 10 and enters the transparent body 20 is repeatedly reflected between the first and second reflecting bodies 10 and 30 and a multiple interference by multiple reflection light takes place and resonates at a particular wavelength satisfying the resonant conditions. By the resonance, light at the resonant wavelength is absorbed and the electric field inside the device is enhanced and the surface enhancing Raman effect can be obtained at the light scattering surface 4s. Since the resonant wavelength changes according to the thickness and the average refractive index of the transparent body 20 as in the first embodiment, a higher surface enhancing Raman effect (for instance, not smaller than 100 times) can be obtained at a wavelength according to these factors.

Further, since being basically the same as the first embodiment except that the first reflecting body 10 is provided with the metal column structure film 17, the Raman spectroscopic device 4 of this embodiment exhibits the same effect as the first embodiment.

Though the case where the first reflecting body 10 comprises a column structure film 17 where a number of substantially parallel columns 17p extend in a non-parallel direction to the surface of the transparent body and the is of metal has been described in this embodiment, the arrangements shown in FIGS. 6 to 10 may be employed.

Figure 6:
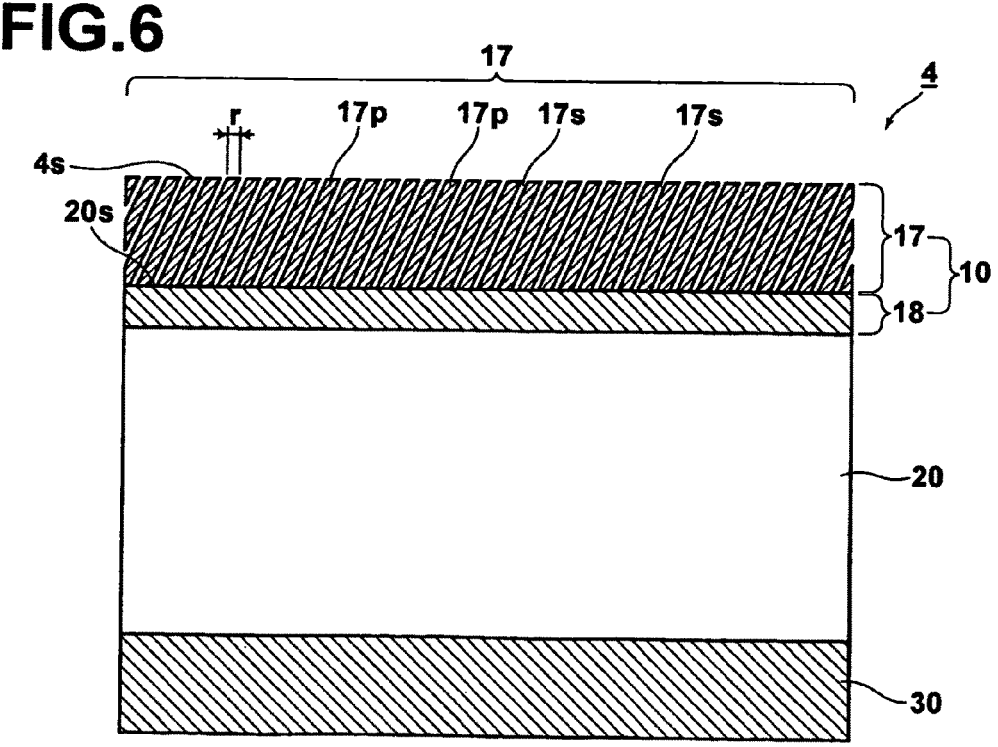
FIG. 6 is a cross-sectional view in the direction of thickness showing a Raman spectroscopic device in another preferred form of a fourth embodiment of the present invention.

As shown in FIG. 6, the arrangement where the first reflecting body 10 has a column structure film 17 and partly reflective film 18 which is formed between the column structure film and the transparent body 20 and exhibits a semi-transmissivity/semi-reflectivity may be employed. With this arrangement, the multiple reflection can be effectively caused in the resonator. As the partly reflective film 18, there can be shown, for instance, metal film and dielectric multi-layered film where a dielectric body such as $MgF_2$, $SiO_2$ and $TiO_2$ are laminated.

FIGS. 7 and 8 show the case where the first reflecting body 10 of a Raman spectroscopic device of FIG. 5 or 6 is further provided with column structure film 17 which is dielectric film and metal film 19 formed on the column structure film 17. Preferably the column structure film is formed by bias sputtering since the dielectric film can be formed more easily as compared with metal film and the metal film can be formed easily along the shape of the column 17p which is a dielectric body when the metal film is formed on the dielectric film having a column structure. In this case, though the metal film 19 formed on the dielectric structural film 17 either includes a column structure or includes no column structure, the metal film 19 is formed substantially holding voids 17s formed in the column structure film 17 which is a dielectric body in either case. When being of a dielectric body, it is preferred that the first reflecting body 10 be of inorganic material which is easy to form film and is excellent in the heat resistance and in the resistance to attack by light. However, for applications where organic material gives rise to no problem, the column structure film 17 may be formed by organic material so long as the growth of the column 17p is excellent. As the method of forming the column structure film 17 when organic material is used, there may be shown plasma chemical deposition method or molecular beam deposition method.

Figure 9:
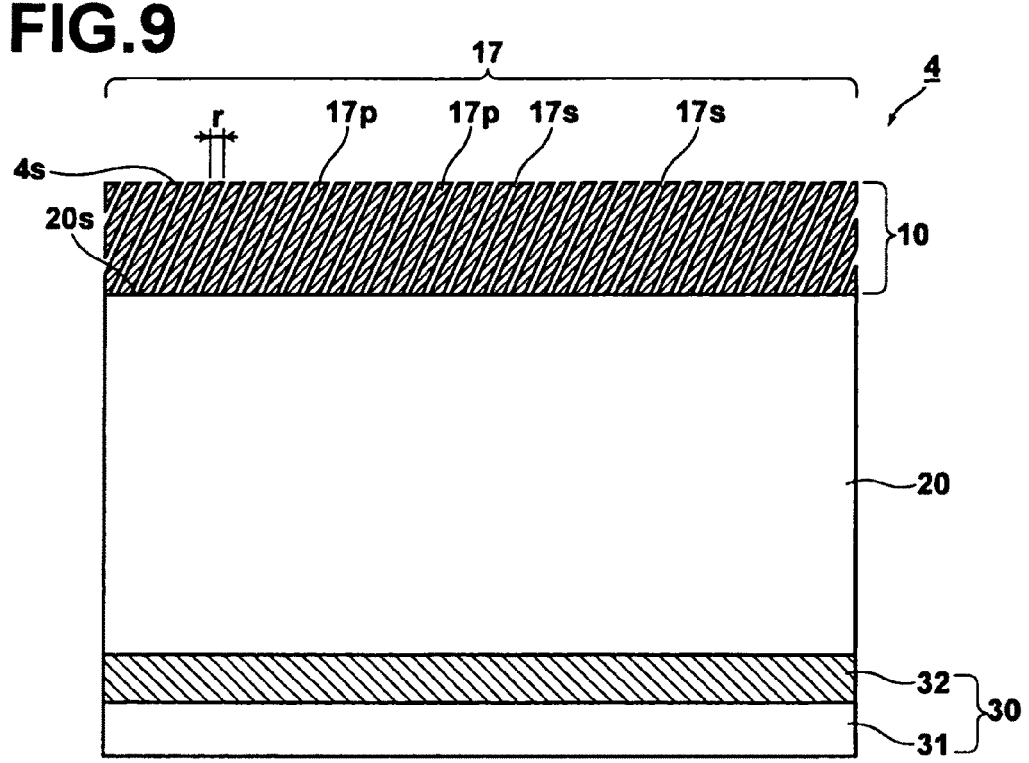
FIG. 9 is a cross-sectional view in the direction of thickness showing a Raman spectroscopic device in still another preferred form of a fourth embodiment of the present invention.
Figure 10:
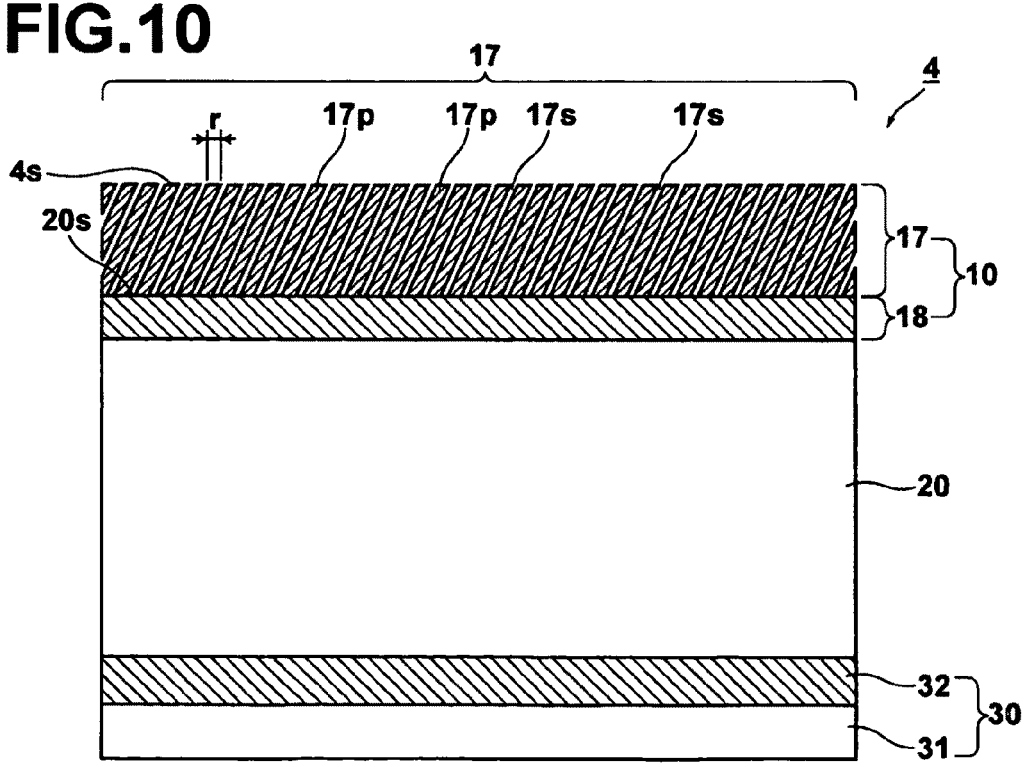
FIG. 10 is a cross-sectional view in the direction of thickness showing a Raman spectroscopic device in still another preferred form of a fourth embodiment of the present invention.

FIGS. 9 and 10 show the case where the second reflecting body 30 of a Raman spectroscopic device of FIG. 5 or 6 is provided with a transparent body 31 and partly reflective film 32 which is formed on the transparent body 31 and exhibits a semi-transmissivity/semi-reflectivity. As the partly reflective film 32, those which are the same as the partly reflective film 18 can be shown. With this arrangement, also the second reflecting body 30 can exhibit a semi-transmissivity/semi-reflectivity and it becomes possible to use light emitted from the second reflecting body 30. The second reflecting body 30 having such an arrangement can be applied to the Raman spectroscopic device of FIG. 7 or 8.

[Example of the Design Change]

In the Raman spectroscopic device of this invention, the first and second reflecting bodies 10 and 30 may be changed in the arrangements thereof and the combination thereof. For example, the Raman spectroscopic device of this invention may be arranged by combining the first reflecting bodies 10 of the first to third embodiments and the second reflecting bodies 30 of the first to third embodiments.

[Raman Spectroscopic System]

Figure 11A:
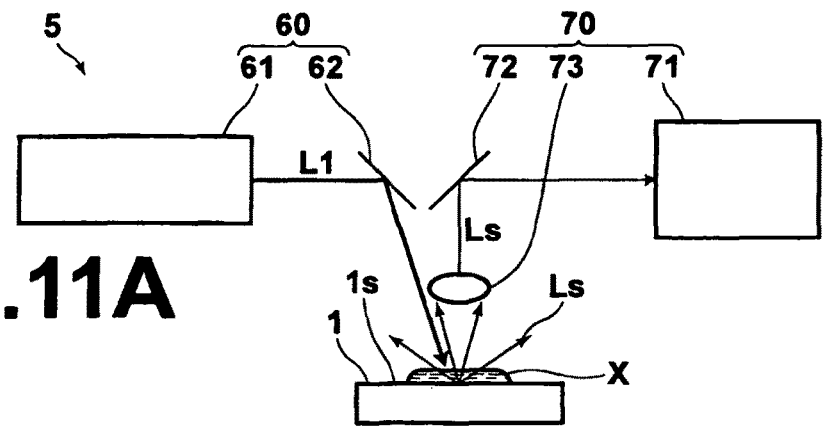
FIG. 11A is a view briefly showing a Raman spectroscopic system in accordance with an embodiment of the present invention.
Figure 11B:
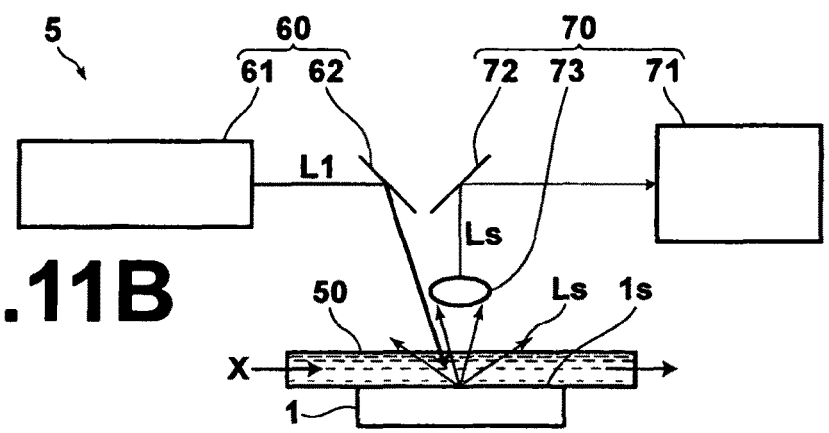
FIG. 11B is a view showing an example of contact of the sample with the Raman spectroscopic device in the Raman spectroscopic system of FIG. 11A.

Raman spectroscopic systems will be described with reference to FIGS. 11A and 11B through the example where the Raman spectroscopic device 1 of the first embodiment described above is employed. FIG. 11A shows a Raman spectroscopic system 5 of an embodiment of the present invention. When the Raman spectroscopic devices 2 to 4 of the second to fourth embodiment is employed, the same structure of the system may be used.

The Raman spectroscopic system 5 of the present embodiment comprises a Raman spectroscopic device 1 of the present invention described above, a light projecting means 60 which projects measuring light L1 of a particular wavelength onto the Raman spectroscopic device 1 and a spectral means 70 which spectroscopically divides scattered light. The light projecting means 60 comprises a mono-wavelength light source 61 such as a laser and an optical waveguide system such as a mirror 62 which guides light emitted from the light source. The light projecting means 60 is arranged to project light of a particular wavelength onto a light scattering surface is of the Raman spectroscopic device 1 with which samples are brought into contact.

The spectral means 70 comprises a spectral detector 71, a collecting lens 73 for collecting divergent light Ls from the sample, an optical waveguide system such as a mirror 72 which guides the divergent light Ls collected by the collecting lens 73 to the spectral detector 71 and spectroscopically divides divergent light Ls generated by the light scattering surface 1s of the Raman spectroscopic device 1 to obtain the Raman spectrum of Raman scattered light. The spectral means 70 is positioned to receive the scattered light generated by the light scattering surface is of the Raman spectroscopic device 1.

In such structure, light at the particular wavelength projected from the light projecting means 60 is scattered on the light scattering surface 1s of the Raman spectroscopic device 1 facing the sample, and the scattered light generated is spectroscopically divided by the spectral means 70 to generate the Raman spectrum. Since the Raman spectrum changes depending on the kind of the sample to be measured, the material can be identified.

For example, when measurement is carried out with a known antibody fixed to the light scattering surface is of the Raman spectroscopic device 1, if an antigen is included in the sample, the obtained Raman spectrum changes due to bonding of the antibody and the antigen. Therefore, the antigen can be identified. Similarly, the antibody can be identified, by fixing a known antigen to the light scattering surface 1s.

In the Raman spectroscopic system 5 of this invention, the sample may be brought into contact in any way, and the sample may be brought into a direct contact with the light scattering surface 1s of the Raman spectroscopic device 1, or may be filled in a sample cell 50 to be brought into contact with the light scattering surface 1s. FIG. 11A shows a form where the sample is brought into a direct contact with the light scattering surface is of the Raman spectroscopic device 1, and FIG. 11B shows a form where the sample is filled in a sample cell 50 and the sample cell 50 is placed on the light scattering surface is of the Raman spectroscopic device 1. Since, FIGS. 11A and 11B are the same in structure except the form in which the sample is brought into contact, the elements analogous to each other are given the same reference numerals in FIGS. 11A and 11B.

The sample cell 50 may be a flow cell, and may be of any suitable material so long as it has a transparent window at an area where the measuring light L1 and the scattered light Ls passes through.

Since the Raman spectroscopic system 5 of this embodiment is formed by the use of the Raman spectroscopic device 1 of this invention and the Raman scattered light is effectively enhanced, data is highly reliable and a precise Raman spectroscopy excellent in data reproduction can be carried out. In the Raman spectroscopic system 5 of this embodiment, since the irregularities on the surface of the Raman spectroscopic device 1 are highly uniform, even if the light projecting place is changed for the same sample, data excellent in reproduction can be obtained. Accordingly, it is possible to increase the reliability of the data by taking a plurality of pieces of data for the same sample in different light projecting places.

Further, in the Raman spectroscopic system 5 of this embodiment, it is preferred that the spectral means 70 receives and spectroscopically divides only the scattered light of the non-direct-reflection components of the measuring light in the light scattering surface 1s. There is a fear that the direct-reflection components is too strong in intensity to excellently detect the Raman spectrum which is intrinsically weak. With such an arrangement, the fear can be overcome and a precise analysis can be carried out.

EMBODIMENTS

Embodiments of the present invention will be described, hereinbelow.

Embodiment 1

Electromagnetic field analysis simulation by the FDTD method was carried out to prove the surface enhancing Raman effect thereof.

As a model for use in the simulation, the Raman spectroscopic device 3 of the third embodiment was employed.

Figure 12:
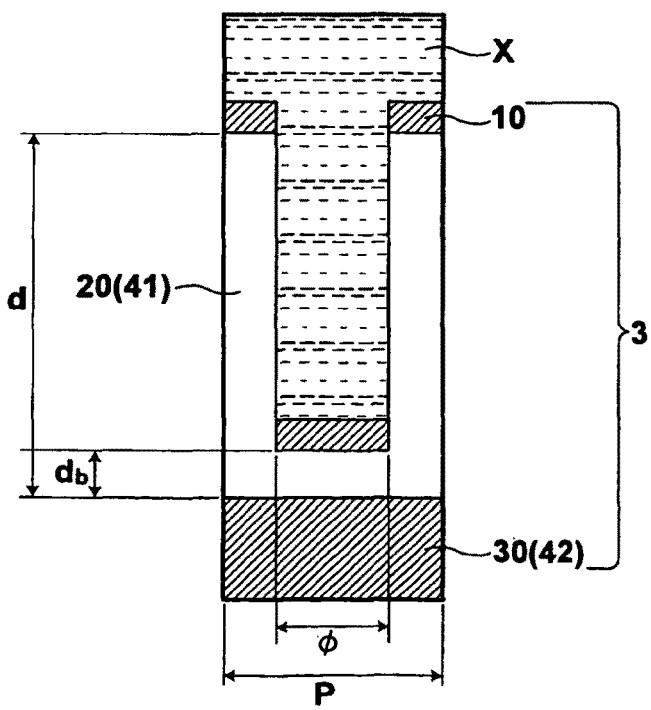
FIG. 12 is an enlarged cross-sectional view showing the Raman spectroscopic device 3 employed as a model of simulation of the embodiment 1.

FIG. 12 is a cross-sectional view in the direction of depth showing the state where a sample x is brought into contact with the Raman spectroscopic device 3 employed as a model, and in FIG. 12, one fine column is shown in an enlarged scale for the purpose of simplicity in viewing the simulating conditions. Elements analogous to those shown in FIG. 3 are given the same reference numerals and are not described.

As shown in FIG. 12, in the Raman spectroscopic device employed as a model, the anodic-oxidized metal (Al) 40=Al, the diameter cp of the fine holes 21=50 nm, pitches P=100 nm, the first reflecting body 10=Au, the thickness of the deposited first reflecting body=20 nm, the thickness d of the transparent metal oxide ($Al_2O_3$) 41=400 nm, and the thickness db of the bottom $Al_2O_3$=20 nm, and metal Au the same as the first reflecting body 10 was deposited on the bottom of the fine holes 21 in the thickness of 20 nm and the sample X in contact with the light scattering surface is was those obtained by dispersing, in water, absorbed material whose refractive index was 1.7.

In the simulation, the intensity distribution of the electric field in the device and the reflectance of the emitted light when mono-wavelength light at an arbitrary wavelength was caused to enter the first reflecting body in substantially perpendicularly thereto were calculated to prove the relation between the resonance and the electric field enhancing effect.

Figure 13A:
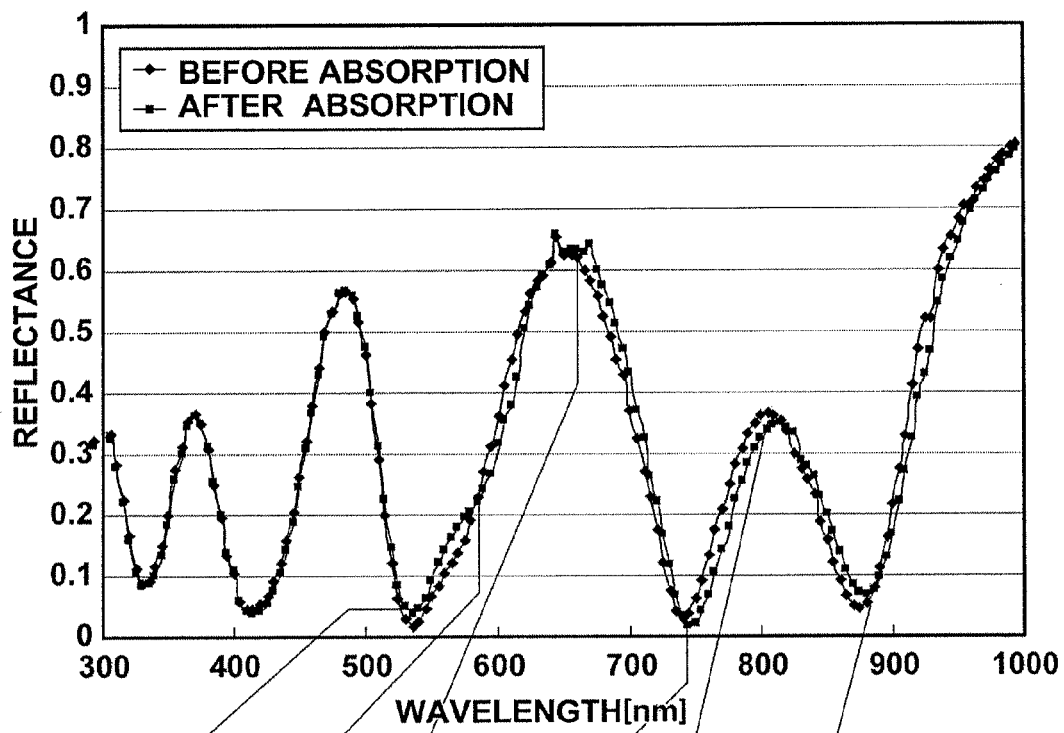
FIG. 13A is a view showing the light emanation/absorption characteristics of embodiment 1.
Figure 13B:
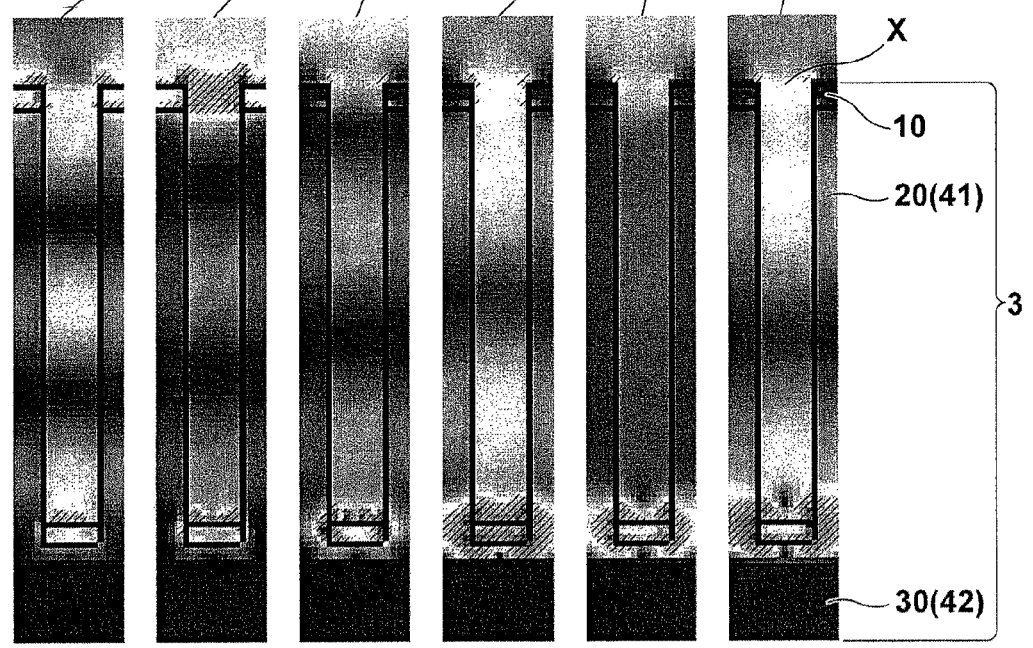
FIG. 13B is a view showing the electric field intensity distribution in the fine hole at the absorption peak wavelength shown in FIG. 13A.

Result of the simulation is shown in FIGS. 13A and 13B. FIG. 13A is a graph where the reflectance of the emitted light from the surface of the device for each wavelength is plotted and represents the absorbing characteristics of the device. FIG. 13B is a schematic view of an intensity distribution of the electric field in the device at the wavelength corresponding to each position of the spectrum shown in FIG. 13A. In FIG. 13B, the more the density of black is, the weaker the electric field is and the thinner the color is, the stronger the electric field is. The region where an especially strong electric field is generated is hatched.

As shown in FIGS. 13A and 13B, in absorption peak wavelengths, the electric field intensifies on the surface of the fine holes or the surface of the Raman spectroscopic device and it has been confirmed that, when the thickness d of the light transmissible fine hole body 41 is 400 nm, the resonance takes place at wavelengths of near 420 nm, 520 nm and 740 nm in a visible region and an effective Raman enhancing effect can be obtained.

Further, at a wavelength of near 740 nm, a local plasmon resonance is generated. When metal is loaded in the bottom of the fine holes 21, the local plasmon resonance is generated both on the first reflecting body 10 and in the bottom of the fine holes 21. It has been confirmed from FIG. 13B that the local plasmon resonance is effectively generated in the bottom of the fine holes 21 in the Raman spectroscopic device which has been employed as the model. Further, it also has been confirmed that the resonant wavelength appears at wavelengths substantially conforming the wavelength which satisfy formula (1).

Embodiment 2

Figure 14:
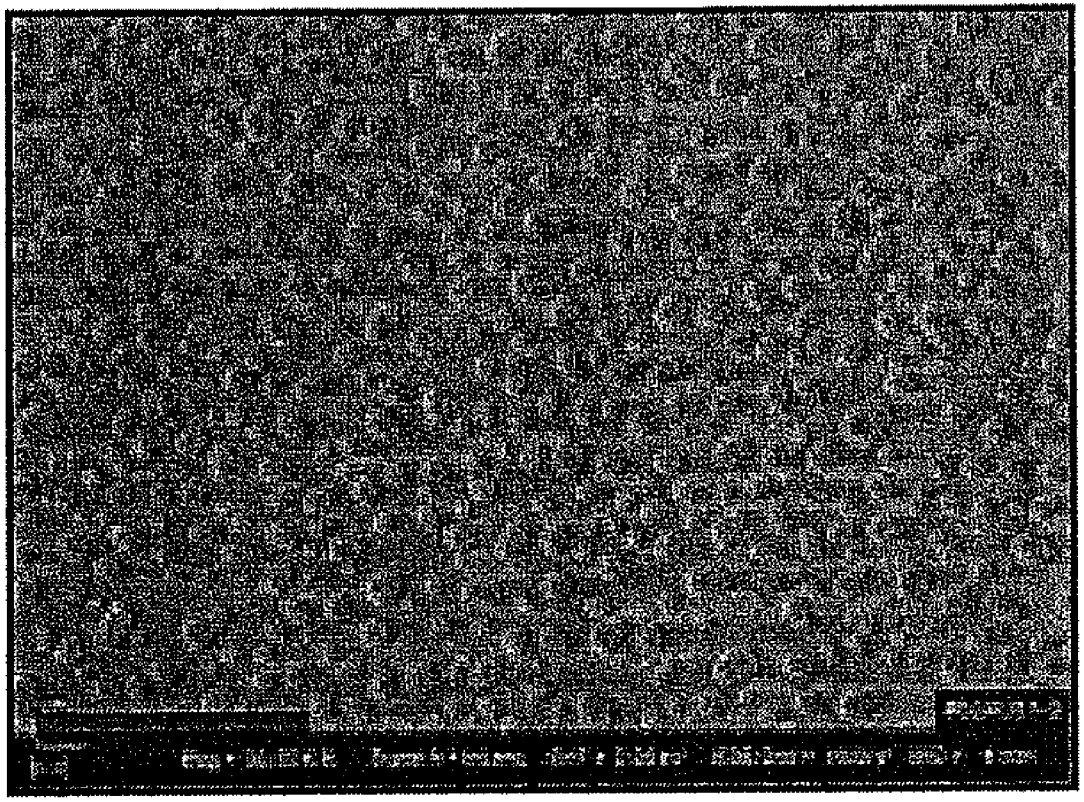
FIG. 14 is an electron micrograph showing the Raman spectroscopic device 2 employed as a model of simulation of the embodiment 2.

Electromagnetic field analysis simulation was carried out by the use of the Raman spectroscopic device 2 of the second embodiment as a model in a manner similar to embodiment 1 to prove the surface enhancing Raman effect thereof. In the Raman spectroscopic device 2, the first reflecting body 10 comprised a metal layer where a plurality of metal particles substantially equal to each other in diameter were substantially regularly arranged in matrix on the surface of transparent body 20. FIG. 14 shows an electron micrograph showing the surface of the first reflecting body 10 of the Raman spectroscopic device 2 employed as a model.

In the Raman spectroscopic device 2 having surface structure shown in FIG. 14 where the first and second reflecting bodies are of gold and aluminum respectively and the thickness of the transparent body d is 220 nm, when mono-wavelength light of an arbitrary wavelength enters the surface of the first reflecting surface in substantially perpendicularly to the first reflecting body, electric field distributions in the direction of the thickness in the surface of the device and the inside thereof and the reflectances in the direction of the thickness in the surface of the device and the inside thereof were calculated to prove the relation between the resonance and the electric field enhancing effect as in the embodiment 1. The sample X in contact with the light scattering surface was the same as in the embodiment 1. Result of the simulation is shown in FIGS. 15 and 16.

Figure 15:
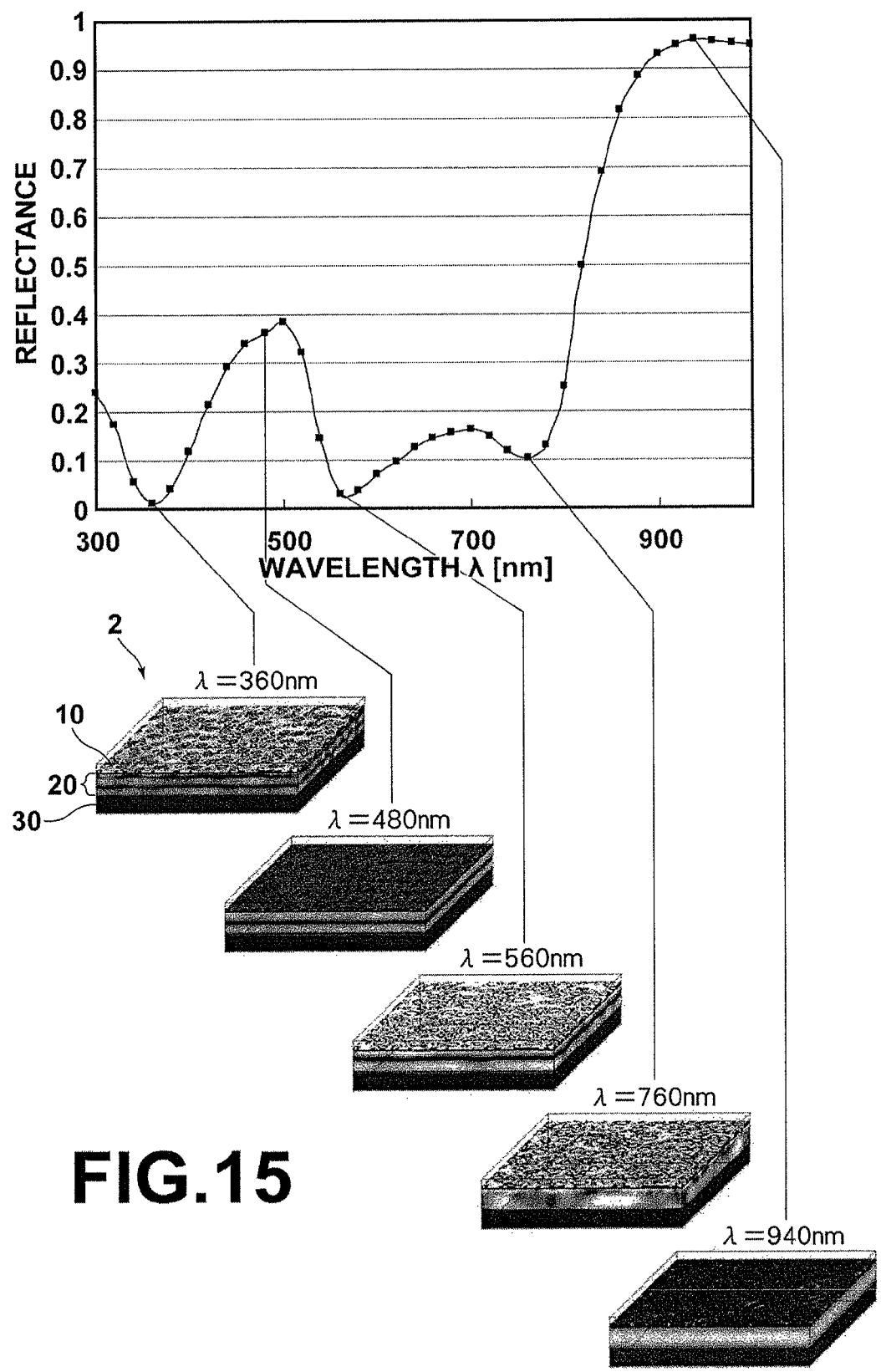
FIG. 15 is a perspective view of the Raman spectroscopic device 2 showing the light emanation/absorption characteristics and the distribution of the electric field intensity in the directions of the surface and the thickness at each absorption peak wavelength of the embodiment 2.

FIG. 15 shows by the use of a perspective view of the Raman spectroscopic device 2 the absorption characteristics of light emanating from the surface of the device, and the distribution of the electric field intensity in directions of the surface and the thickness of the Raman spectroscopic device 2 as in the embodiment 1. Since the arrangement of the Raman spectroscopic device 2 employed as a model in FIG. 15 is shown in FIG. 2, elements analogous to those shown in FIG. 2 are given the same reference numerals and are not described.

Figure 16:
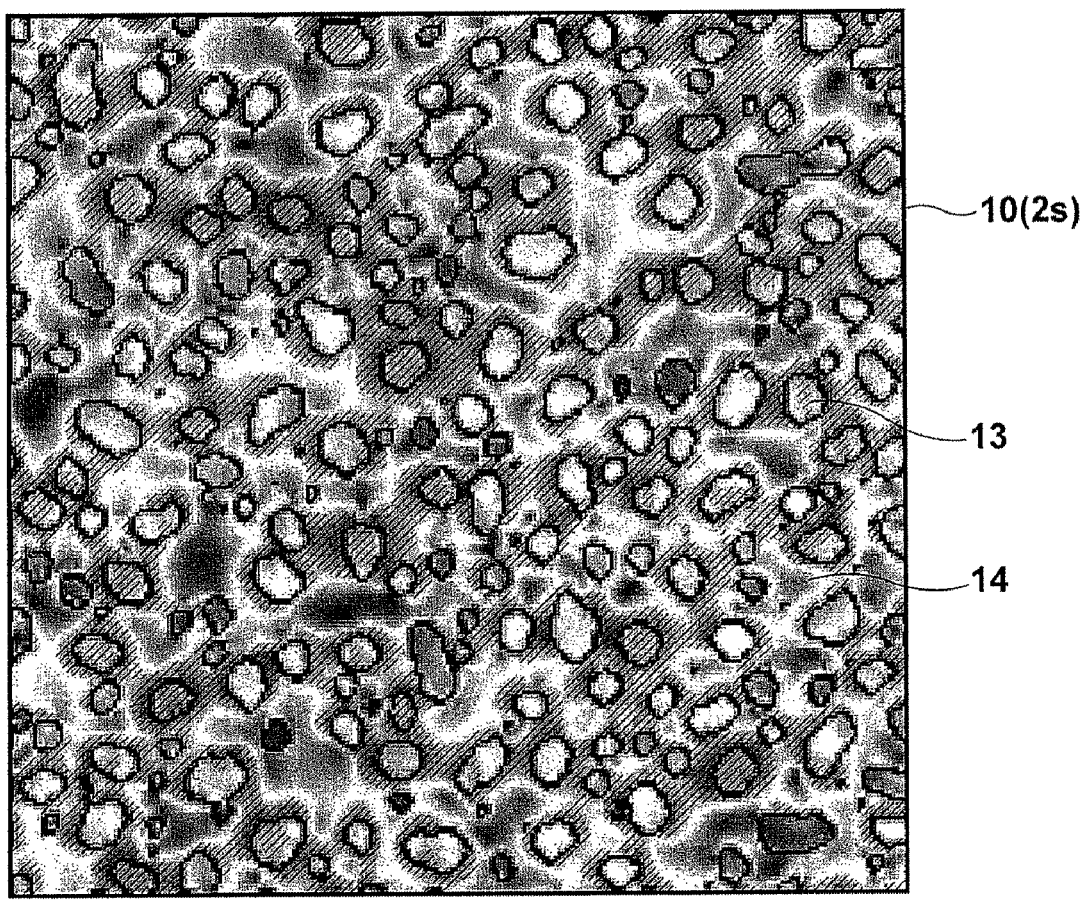
FIG. 16 is a plan view of the Raman spectroscopic device 2 showing the distribution of the electric field intensity at the local plasmon resonance wavelength.

FIG. 16 shows the distribution of the electric field intensity at the local plasmon resonance wavelength when the surface (corresponding to the perspective view at λ=760 nm in FIG. 15) of the Raman spectroscopic device 2 is viewed in plan. In FIGS. 15 and 16, the more the density of black is, the weaker the electric field is while the thinner the color is, the stronger the electric field is and the region where an especially strong electric field is generated is hatched, as in the embodiment 1.

In FIG. 15, since the thickness d of the transparent body 20 is not larger than 300 nm as described above, the resonance wavelength in a visible region is a single and only 560 nm. Absorption at 760 nm is due to the local plasmon resonance. As shown in FIG. 15, it has been confirmed that the electric field on the surface of the Raman spectroscopic device is effectively enhanced at any of the absorption peak.

Further, it also has been confirmed that the resonance takes place at a wavelength where the electric field intensifies near the surface. Further, it has been confirmed from FIG. 16 that the electric field is effectively enhanced near the metal particles forming the first reflecting body 10.

The technic of the present invention can be applied to the Raman spectroscopic system where scattered light obtained by projecting mono-wavelength light onto material is spectroscopically divided to obtain the Raman spectrum and is employed for, for instance, identification of the material.

The invention claimed is:

1. A Raman spectroscopic device for use in Raman spectroscopy, in which a measuring light beam of a particular wavelength is irradiated onto a sample in contact with a light scattering surface, Raman scattered light generated at the light scattering surface is spectrally decomposed, and is employed for detecting a detection target substance in the sample, in the form of an optical resonator, comprising:
   a first reflecting body that exhibits semi transmissivity/ semi reflectivity and has a surface which is the light scattering surface for generating Raman scattering;
   a transparent body; and
   a second reflecting body that exhibits reflectivity, laminated in sequence one on another;
   whereby the intensity of the Raman scattered light is amplified by the amplified electric field at the light scattering surface by light absorption, generated by resonance in the optical resonator upon irradiation of the measuring light beam, wherein:
   the first reflecting body has a structure of protrusions and recesses, which are smaller than the wavelength of the measuring light beam to be irradiated onto the light scattering surface.

2. A Raman spectroscopic device as defined in claim 1, wherein:
   the first reflecting body is a metal layer formed in a pattern on the surface of the transparent body.

3. A Raman spectroscopic device as defined in claim 1, wherein
   the first reflecting body is a metal layer comprising a plurality of non-aggregate metal particles which are fixed to the surface of the transparent body.

4. A Raman spectroscopic device as defined in claim 1, wherein:
   the transparent body is a transparent finely apertured body having a plurality of fine apertures which are open in a surface facing the first reflecting body and of which the diameters are smaller than the wavelength of the measuring light beam in diameter; and
   the first reflecting body is a metal layer having a plurality of fine apertures along the shape of the surface of the transparent body.

5. A Raman spectroscopic device as defined in claim 4, wherein:
   the transparent finely apertured body is a metal oxide body obtained by anodic oxidization of a part of a metal body;
   the second reflecting body is a non anodic oxidized part of the anodic oxidized metal body; and
   the first reflecting body is a metal layer formed as a film on the transparent body.

6. A Raman spectroscopic device as defined in claim 4, wherein:
   at least a portion of the plurality of fine apertures of the transparent finely apertured body is filled with metal.

7. A Raman spectroscopic device as defined in claim 6, wherein:
   the bottoms of the plurality of fine apertures of the transparent finely apertured body are filled with metal.

8. A Raman spectroscopic device as defined in claim 1, wherein the first reflecting body comprises:
   a metal column structured film having a number of substantially parallel columns extending in a direction not parallel to the surface of the transparent body.

9. A Raman spectroscopic device as defined in claim 1, wherein the first reflecting body comprises:
   a dielectric column structured film having a number of substantially parallel columns extending in a direction not parallel to the surface of the transparent body; and
   a metal film formed on the dielectric column structure film.

10. A Raman spectroscopic apparatus, comprising:
    a Raman spectroscopic device as defined in claim 1;
    a light irradiating means for irradiating a measuring light beam of a particular wavelength onto the light scattering surface of the Raman spectroscopic device; and
    a spectral means for spectrally decomposing the light scattered by the light scattering surface, thereby obtaining the spectrum of Raman scattered light.

11. A Raman spectroscopic apparatus as defined in claim 10, wherein:
    the spectral means receives and spectrally decomposes only scattered light of non directly reflected components of the measuring light beam scattered at the light scattering surface.

* * * * *